(12) United States Patent
Kadowaki et al.

(10) Patent No.: US 7,850,976 B2
(45) Date of Patent: Dec. 14, 2010

(54) INSULIN RESISTANCE IMPROVING AGENTS

(75) Inventors: Takashi Kadowaki, Kanagawa (JP); Toshimasa Yamauchi, Tokyo (JP); Junji Kamon, Tokyo (JP); Hironori Waki, Kanagawa (JP); Ryozo Nagai, Tokyo (JP); Satoshi Kimura, Tokyo (JP); Motoo Tomita, Kanagawa (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 326 days.

(21) Appl. No.: 12/041,279

(22) Filed: Mar. 3, 2008

(65) Prior Publication Data

US 2010/0120674 A1    May 13, 2010

Related U.S. Application Data

(62) Division of application No. 10/502,051, filed as application No. PCT/JP02/07599 on Jul. 26, 2002, now abandoned.

(30) Foreign Application Priority Data

Jan. 31, 2002    (JP) .............................. 2002-023554

(51) Int. Cl.
*A61K 38/22* (2006.01)
*A61K 39/00* (2006.01)
*A61K 45/00* (2006.01)
*A61K 48/00* (2006.01)

(52) U.S. Cl. ........................ 424/198.1; 514/12; 530/399

(58) Field of Classification Search ........................ None
See application file for complete search history.

(56) References Cited

U.S. PATENT DOCUMENTS 6,566,332 B2 *  5/2003  Fruebis et al. ................. 514/12

2006/0166873 A1    7/2006  Kadowaki et al.

FOREIGN PATENT DOCUMENTS

| WO | 96/39429 | 12/1996 |
|---|---|---|
| WO | WO/96/39429 | * 12/1996 |

OTHER PUBLICATIONS

Joachim Fruebis, et al., "Proteolytic cleavage product of 30-kDa adipocyte complement-related protein increases fatty acid oxidation in muscle and causes weight loss in mice", PNAS, vol. 98, No. 4, Feb. 13, 2001, pp. 2005-2010.
Yamauchi T. et al., The fat-derived hormone adiponectin reverses insulin resistance associated with both lipoatrophy and obesity, Nat Med., vol. 7, No. 8, 2001, pp. 941-946.
Toshimasa Yamauchi et al., "Adiponectin ni yoru 2 Gata Tonyobyo no Insulin Teikosei no Kaizen," Experimental Medicine, vol. 19, No. 17, 2001, pp. 2301-2305 (with Partial English Translation).
Haruhiko Osawa, et al., "2 Gata Tonyobyo Kanren Idenshi Gun no Kaimei," Protein, Nucleic Acid and Enzyme, vol. 46, No. 16, 2001, pp. 2332-2336 (with Partial English Translation).
Kazuo Hara et al., "Seikatsu Shukanbyo no Taylor Made Iryo," Igaku no Arumi, vol. 197, No. 13, 2001, pp. 1046-1048 (with Partial English Translation).
U.S. Appl. No. 12/041,279, filed Mar. 3, 2008, Kadowaki, et al.
U.S. Appl. No. 12/173,244, filed Jul. 15, 2008, Kadowaki, et al.

* cited by examiner

*Primary Examiner*—Gary B. Nickol
*Assistant Examiner*—Elly-Gerald Stoica
(74) *Attorney, Agent, or Firm*—Oblon, Spivak, McClelland, Maier & Neustadt, L.L.P.

(57) ABSTRACT

The invention provides an insulin resistance improving agent and a therapeutic agent for type 2 diabetes, which contain a C-terminal globular domain of adiponectin, adiponectin, or a gene for the domain or adiponectin. The invention also provides a method for improving insulin resistance and treating type 2 diabetes by administering the aforementioned agent(s).

14 Claims, 17 Drawing Sheets

HX531:   −           +

INSULIN RESISTANCE IMPROVING AGENTS

The present application is a divisional of U.S. Ser. No. 10/502,051 (now abandoned), filed on Jul. 30, 2004, which is a National Stage (371) of PCT/JP02/07599, filed on Jul. 26, 2002, which claims priority to JP 2002-23554, filed on Jan. 31, 2002.

TECHNICAL FIELD

The present invention relates to an insulin resistance improving agent useful for the prevention and treatment of obesity, diabetes, and cardiovascular diseases, as well as to a drug for treating type 2 diabetes.

BACKGROUND ART

Hitherto, adipose tissue has been considered a mere storage medium for excess energy. However, recent research has elucidated that adipose tissue produces and secretes a variety of physiologically active substances. The physiologically active substances are collectively called adipocytokines, and specific members which have been known to date include leptin, tumor necrosis factor-$\alpha$ (TNF-$\alpha$), plasminogen-activator inhibitor type 1 (PAI-1), adipsin, and resistin. Some of these adipocytokines, such as leptin, TNF-$\alpha$, and resistin, have been suggested to be secreted from adipocytes to thereby control sensitivity to insulin.

Adiponectin has recently been identified as an adipocytokine. Adiponectin was originally identified independently by four research groups that used different approaches. Adiponectin cDNA was isolated by large-scale random sequencing of a 3'-directed, human-adipose-tissue cDNA library. Mouse cDNAs for adiponectin termed AcrpSO and AdipoQ were cloned through differential display before and after differentiation of mouse 3T3-L1 and 3T3-F442A cells, respectively. Human adiponectin was also purified from plasma as gelatin-binding protein 28. Obese/diabetic mice and humans exhibit significantly reduced levels of mRNA expression of adiponectin and plasma adiponectin. Lodish et al. have recently reported that a proteolytic cleavage product of Acrp30 increases fatty-acid oxidation in muscle and causes weight loss in mice.

However, whether or not adiponectin is effective in the actual treatment of diabetes remains unknown.

Insulin resistance induced by high-fat diet and accompanied with obesity is a major risk factor for diabetes and cardiovascular diseases, and therefore, capacity to improve insulin resistance is a key factor for determining that a certain drug is effective for the treatment of diabetes.

Accordingly, an object of the present invention is to provide a novel drug which improves insulin resistance and thus is useful in the treatment of diabetes.

DISCLOSURE OF THE INVENTION

The present inventors have investigated effects of adiponectin through use of model mice of different types; i.e., mice in which insulin sensitivity had been modified, obese mice, and type 2 diabetes mice, and have found that decrease in expression or loss of expression of adiponectin is a cause for development of insulin resistance, and that administration of adiponectin or a fragment of adiponectin, or introduction of any of their genes, is effective for the treatment of insulin-resistant diabetes and type 2 diabetes, thereby leading to completion of the invention.

Accordingly, the present invention provides an insulin resistance improving agent containing, as an active component, a C-terminal globular region, adiponectin, or a gene for the globular region or adiponectin.

The present invention also provides a therapeutic drug for type 2 diabetes, containing, as an active component, a C-terminal globular region, adiponectin, or a gene for the globular region or adiponectin.

BEST MODE FOR CARRYING OUT THE INVENTION

Figure 1:
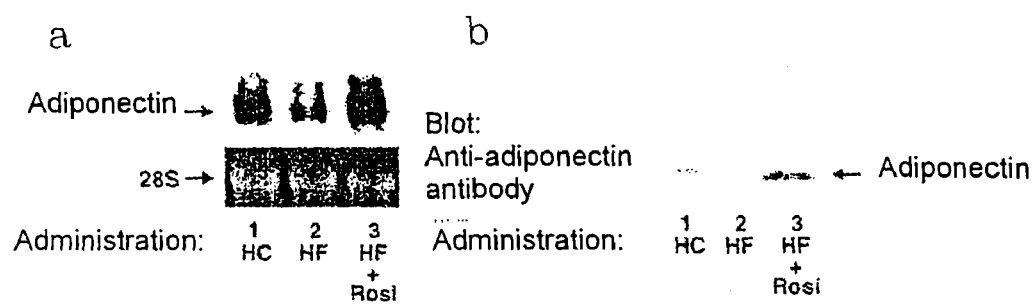
FIG. 1 shows the amounts of adiponectin mRNA in WAT (a) and serum adiponectin levels (b) of db/db mice.

Adiponectin to be used in the present invention has already been cloned [Maeda, K. et al., Biochem. Biophys. Res. Commun. 221, 286-296 (1996), Nakano, Y. et al., J. Biochem. (Tokyo) 120, 802-812 (1996)], and therefore, is available through known means. SEQ ID NOs: 1 and 2 show the amino acid sequence and the nucleotide sequence of human adiponectin, respectively. Adiponectin consists of an N-terminal collagen-like domain (cAd) and a C-terminal globular domain (gAd; in SEQ ID NO: 1, amino acid Nos. 114 to 239 or 111 to 242). The C-terminal globular domain (gAd) is highly preferred, as it provides stronger effect in alleviating high blood sugar and hyperinsulinemia. SEQ ID NOs: 3 and 4 show the amino acid sequence and nucleotide sequence of mouse adiponectin, respectively. The cAd domain of mouse adiponectin extends from the 45th to 109th amino acid residues, and the gAd domain of the same extends from the 110th to 247th amino acid residues. Also, proteins that can be employed in the present invention are not limited to a protein having any of amino acid sequences of SEQ ID NOs: 1 to 4 or a protein having an amino acid sequence exhibiting the gAd domain; any other protein may be employed, even though it is a protein derived therefrom through substitution, deletion, or addition of one or more amino acid residues, so long as it exhibits effects equivalent to those of adiponectin. Examples of the amino acid sequence derived through substitution, deletion, or addition of one or more amino acid residues in the amino acid sequence include those sequences having 80% or more homology, more preferably 90% or more homology, to the sequence of SEQ ID NO: 1.

Examples of genes which may be used in the present invention include a gene encoding adiponectin of SEQ ID NO: 1, and a gene encoding gAd. Moreover, genes having a nucleotide sequence capable of being hybridized with any of these genes under stringent conditions may also be used.

A polypeptide of adiponectin or a portion thereof may be separated from the cells containing it. However, since a cloned gene capable of encoding adiponectin has already become available, the polypeptide may be prepared by means of the DNA recombinant technique. Specifically, an expression vector is prepared by use of the gene, and the vector is used to create transformant cells.

As shown in the Examples provided hereinbelow, model mice in which insulin sensitivity had been modified were found to exhibit a reduction in expression of adiponectin and development of insulin resistance simultaneously. Adiponectin reduces insulin resistance by lowering the triglyceride content of the muscles and the liver of an obese mouse. This mechanism is based on an elevated expression of a molecule which participates in both burning of fatty acids and energy consumption in the muscles. Also, the insulin resistance in lipoatrophic mice was alleviated by single use of either adiponectin or leptin. However, when adiponectin and leptin were used in combination, full alleviation was attained. In any of obese model mice and lipoatrophic model mice, reduced adiponectin participates in the manifestation of insulin resistance. Therefore, adiponectin has thus been proven to serve as a new type of remedy for alleviation of insulin resistance and treatment of type 2 diabetes.

When the drug of the present invention is administered to mammals including humans, a pharmacologically acceptable carrier may be added to the aforementioned active component, thereby forming pharmaceutical compositions suitable for different manners of administration. A preferred manner of administration is injection. Examples of the pharmacologically acceptable carrier include distilled water, a solubilizer, a stabilizer, an emulsifier, and a buffer. The dose of any of the drugs differs depending on the pathological condition, sex, body weight, etc. of the patient, and may be approximately 0.1 µg to 10 mg/day as reduced to the amount of adiponectin.

EXAMPLES

The present invention will next be described in more detail by way of Examples, which should not be construed as limiting the invention thereto.

A. Methods (1) Chemicals

Rosiglitazone (PPAR-γ agonist) and HX531 (PPAR-γ/RXR inhibitor) were synthesized as described in the literature (Chem. Pharm. Bull. (Tokyo) 47, 1778-1786 (1999), Diabetes 47, 1841-1847 (1998)).

(2) Animals

PPAR-γ$^{+/-}$ mice were prepared in a manner which had already been reported (Mol. Cell. 4, 597-609 (1999)). All other animals were purchased from Nippon CREA. Six-week-old mice were fed powdered chow, and drugs were given as feed admixtures as described (Mol. Cell. 4, 597-609 (1999)).

(3) RNA Preparation, Northern-Blot Analysis, and Immunoblotting

Total RNA was prepared from tissues through use of TRIzol (GIBCO-BRL) according to the manufacturer's instructions. RNA obtained from 5 to 10 mice in each group was pooled, and aliquots were subjected to northern blot analysis with the probes for rat ACO (from T. Hashimoto), mouse CD36, UCP2, PPAR-α (from K. Motojima), or mouse adiponectin cDNA (J. Biol. Chem. 273, 16710-16714 (1998), Diabetes 47, 1841-1847 (1998)). The radioactivity in each band was quantified, and fold change in each mRNA was calculated after correction for loading differences by measuring the amount of 28S rRNA. Serum adiponectin levels were determined by immunoblotting with the polyclonal antibody against gelatin-binding protein 28 (raised against the peptide of CYADNDNDSTFTGFLLYHDTN, which corresponds to the C-terminal 20 amino acid residues of human adiponectin with an extra cysteine at its N terminus) through use of a recombinant adiponectin as standards (J. Biochem. (Tokyo) 120, 802-812 (1996)). The procedures used for immunoprecipitation and immunoblotting have been described (Mol. Cell. Biol. 16, 3074-3084 (1996)). The data from one of three independent experiments are shown as representative data.

(4) Blood Sample Assays

Plasma glucose, serum FFA, and triglyceride levels were determined through a glucose B-test, nonesterified fatty acid (NEFA) C-test, and triglyceride L-type (Wako Pure Chemicals), respectively. Plasma insulin was measured by insulin immunoassay (Morinaga Institute of Biological Science) (Diabetes 47, 1841-1847 (1998)). Leptin was assayed with an ELISA-based Quantikine M mouse leptin immunoassay kit (R&D Systems) according to the manufacturer's instructions.

(5) Generation of 6×His-Adiponectin Fusion Proteins.

Each of full-length mouse adiponectins, cAd and gAd, was introduced into the pQE-30 bacterial expression vector (Qiagen). The expression of histidine-tagged adiponectins, cAd and gAd, in JM-109 was induced by the addition of isopropyl β-thiogalactopyranoside to growth medium. Bacterial extracts were prepared using standard methods, and the fusion proteins were purified by elution by use of a nickel-ion agarose column (Diabetes 47, 1841-1847 (1998)). ActiClean Etox affinity columns (Sterogene Bioseparations) were used to remove potential endotoxin contaminations.

(6) Administration of Adiponectin or Leptin

Adiponectin or leptin was administered to mice through intraperitoneal injection or continuous systemic infusion as described (Nature 401, 73-76 (1999)). An Alzet micro-osmotic pump (model 1002, Alza) was inserted subcutaneously in the back of each mouse. A daily dose (shown in Figures) of recombinant leptin (Sigma) or adiponectin was dissolved in a total volume of 0.1 mL of PBS, and the solution was delivered to mice through the pump for twelve days.

(7) Insulin-Resistance Index

The areas of glucose and insulin curves were calculated by multiplying the cumulative mean height of the glucose values (1 mg/ml=1 cm) and insulin values (1 ng/ml=1 cm), respectively, by time (60 min=1 cm) (Am. J. Physiol. 240, E482-488

(1981)). The insulin resistance index was calculated from the product of the areas of glucose and insulin×$10^{-2}$ in glucose tolerance test (Mol. Cell. 4, 597-609 (1999)). The results are expressed as the percentage of the value of each control.

(8) Lipid Metabolism and Enzymatic Activity of ACO

The measurements of [$^{14}$C] $CO_2$ production from [1-$^{14}$C] palmitic acid were performed using liver and muscle slices as described (Diabetes 47, 1841-1847 (1998)). Liver and muscle homogenates were prepared, and tissue triglyceride content was determined with an extract solution ($CHCl_3$:$CH_3OH$=2:1). The remainder of the liver and muscle was immediately frozen in liquid nitrogen and stored at −80° C. until measurement of the enzymatic activity of ACO. ACO activity in the light mitochondrial fraction of liver and muscle was measured by assay that was based on the $H_2O_2$ dependent oxidation of leuco-dichlorofluorescein (Diabetes 47, 1841-1847 (1998)).

B. Results (1) Relationship Between Adiponectin Expression and Insulin Sensitivity Because adiponectin is reported to be decreased in obesity, we investigated the role of altered adiponectin expression in obesity and insulin resistance. To this end, we used the PPAR-γ agonist, rosiglitazone, which promotes adipogenesis and reduces insulin resistance.

Figure 2A:
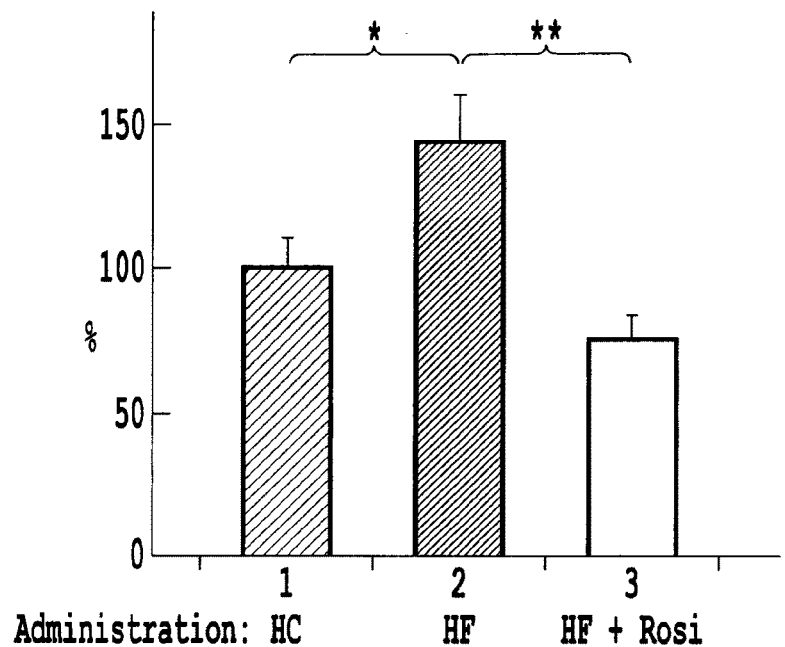
FIG. 2 shows the calculated areas under (a) the glucose curves and (b) the insulin curves obtained through a glucose tolerance test of db/db mice.
Figure 2B:
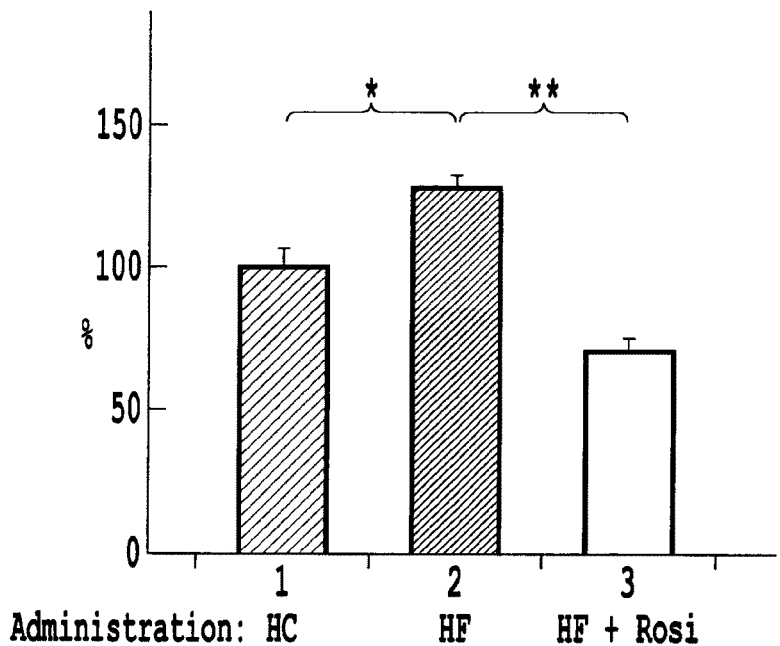
Figure 3:
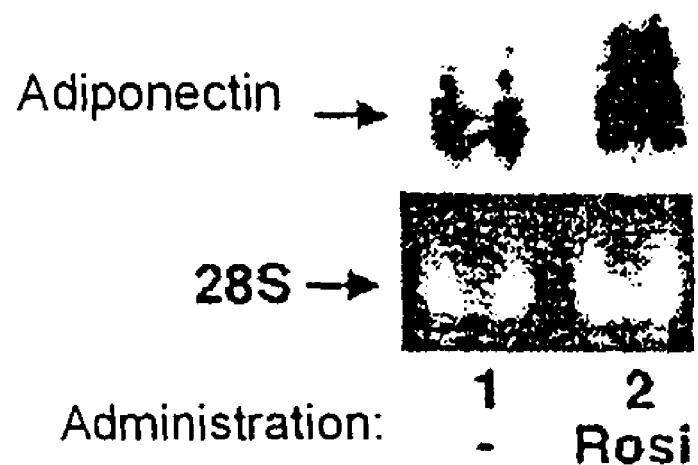
FIG. 3 shows the amounts of adiponectin mRNA in 3T3L1 adipocytes.

The results are shown in FIGS. 1, 2, and 3. FIG. 1 shows amounts of the adiponectin mRNA in WAT (FIG. 1a) or serum levels of adiponectin (FIG. 1b) of db/db mice on the high-carbohydrate diet (HC), on the high-fat diet (HF), or on the high-fat diet and treated with rosiglitazone (HF+Rosi).

FIG. 2 shows values of area under the glucose curve (FIG. 2a) and area under the insulin curve (FIG. 2b) obtained through a glucose tolerance test of db/db mice which had been subjected to the high-carbohydrate diet (HC), to the high-fat diet (HF), or to the high-fat diet and treated with rosiglitazone (HF+Rosi). Results are expressed as the percentage of the value based on that of untreated mice on the HC diet. The basal glucose levels (time=0 of the glucose tolerance test) of untreated db/db mice on the HC diet were 244.8±23.3 mg/dl (FIG. 2a). Each bar represents the mean±s.e. (n=5-10) (*, P<0.05; **, P<0.01; compared with untreated mice on the HC diet).

FIG. 3 shows amounts of adiponectin mRNA in 3T3L1 adipocytes which were untreated (−) or treated with 1 μM rosiglitazone (Rosi) for 24 hours.

A high-fat diet reduced the mRNA levels in white adipose tissue (WAT) (FIG. 1a) and serum levels of adiponectin (FIG. 1b) in mice with hyperglycemia (FIG. 2a) and hyperinsulinemia (FIG. 2b). Rosiglitazone significantly increased the mRNA levels in WAT (FIG. 1a) and serum levels of adiponectin (FIG. 1b) in mice on high-fat diet, and, at the same time, ameliorated hyperglycemia (FIG. 2a) and hyperinsulinemia (FIG. 2b). There was, however, a slight increase in adipose tissue mass (vehicle: 2.72±0.11 g; Rosi: 2.84±0.16 g) and body weight (vehicle: 46.5±0.70 g; Rosi: 47.9±1.0 g) in db/db mice. In the case of wild-type controls (C57) also, similar results were obtained. In differentiated 3T3L1 adipocytes in vitro, rosiglitazone also increased adiponectin expression (FIG. 3c). These data raise the possibility that the expression of adiponectin mRNA might be partially regulated by a PPAR-γ-dependent pathway, and more closely related to regulation of insulin sensitivity than obesity.

(2) Relationship Between Depletion of Adipose Tissue and Adiponectin

To clarify the causal relationship between adiponectin expression and insulin sensitivity, we attempted to deplete adipose tissue and hence adiponectin. We developed a mouse model without adipose tissue by severely reducing PPAR-γ/RXR activity (FIGS. 4 to 8).

While PPAR-γ$^{+/-}$ mice were treated with HX531 for six weeks (+) or untreated (−), recombinant full-length adiponectin (Ad), gAd, or leptin (Lep) was administered to each mouse at a predetermined dose (μg/day). Unless otherwise described herein, administration was performed through continuous systemic infusion (pump) in combination with a high-fat (HF) diet for the final twelve days of the six-week HX531 treatment.

Figure 4:
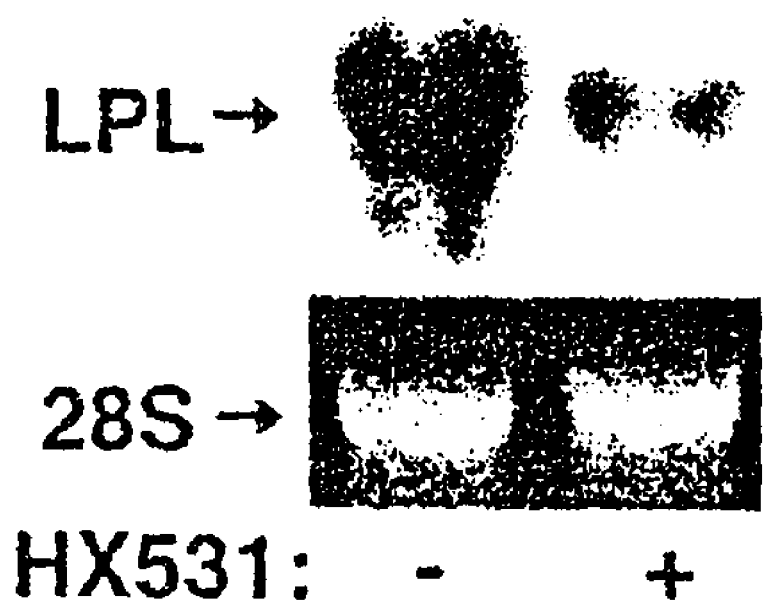
FIG. 4 shows the amounts of LPL mRNA in WAT.
Figure 5:
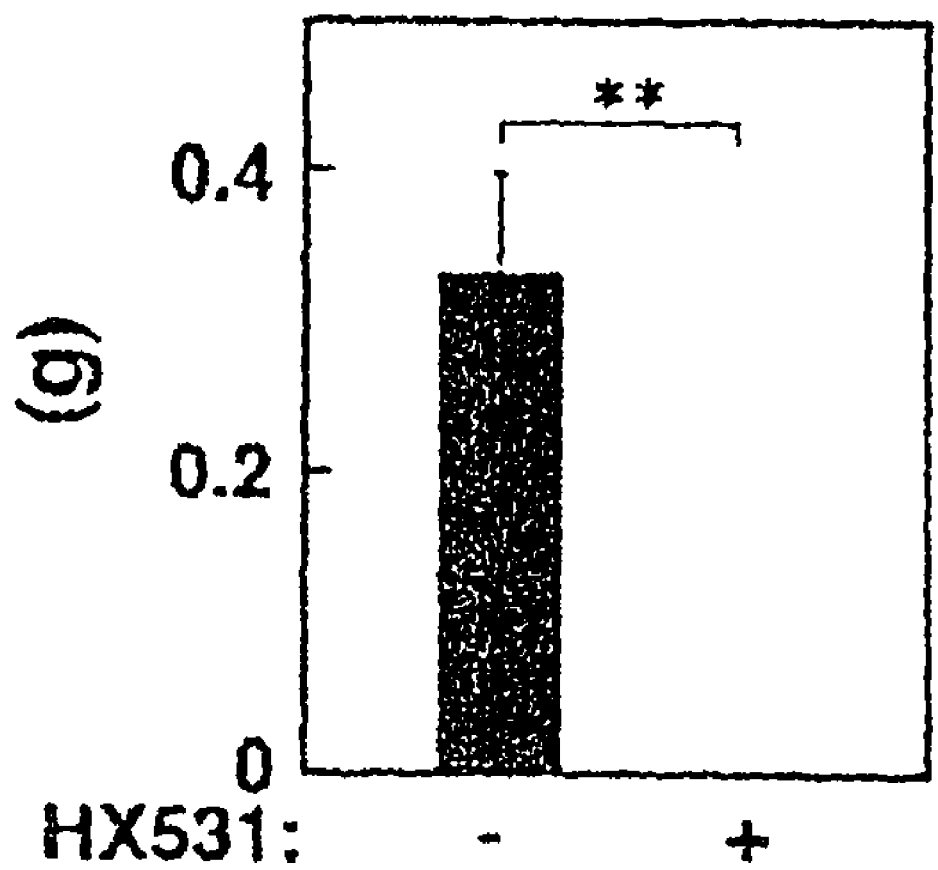
FIG. 5 is a graph showing the epididymal WAT weight.
Figure 6:
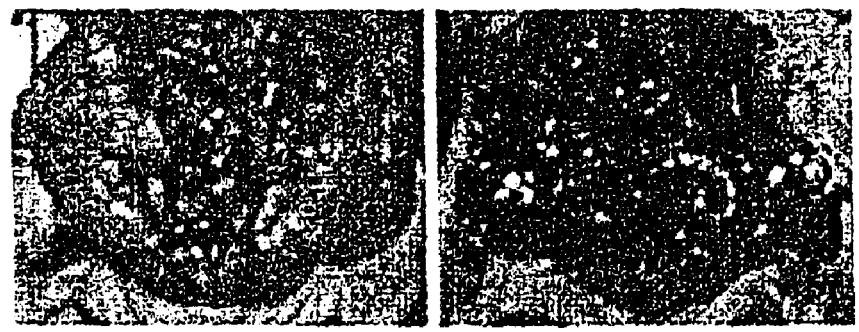
FIG. 6 shows images of the abdominal cavities of mice, which show loss of WAT.
Figure 7:
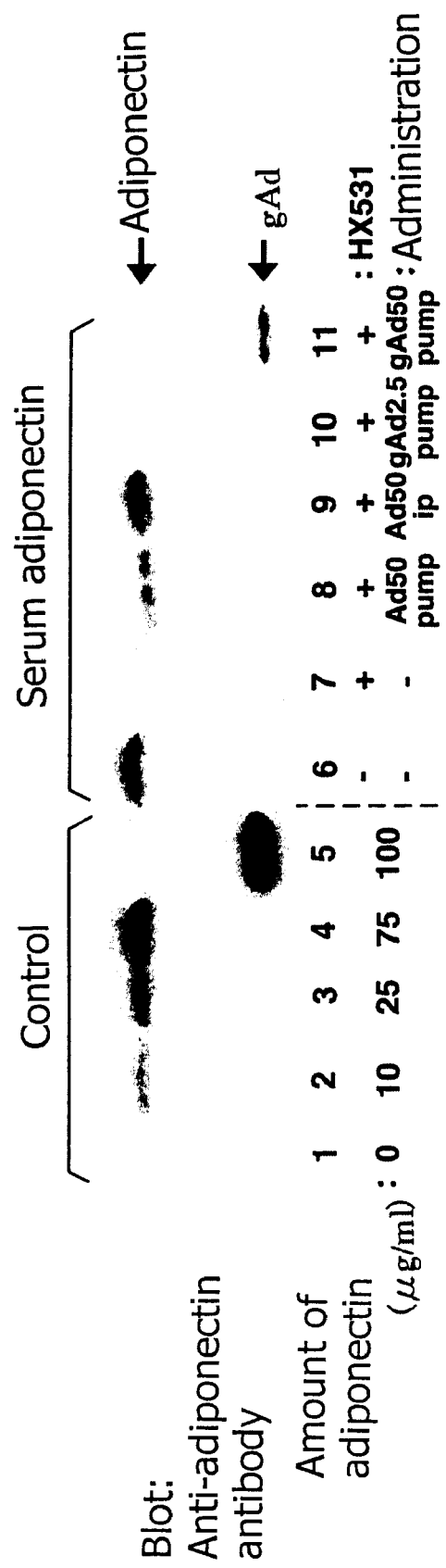
FIG. 7 shows the results of immunoblotting through use of anti-adiponectin antibody.
Figure 8:
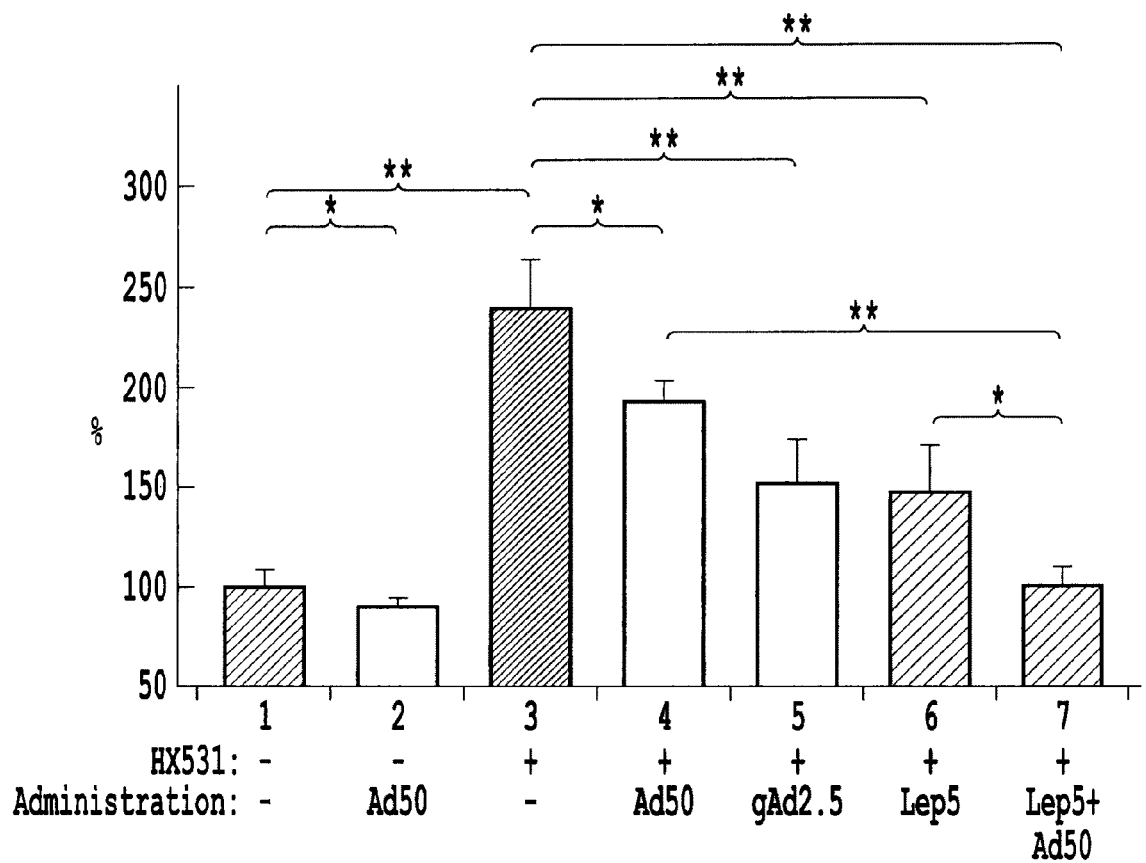
FIG. 8 shows insulin resistance indices.

FIG. 4 shows amounts of LPL mRNA in WAT. FIG. 5 shows epididymal WAT weight. FIG. 6 presents images of the abdominal cavities of the mice illustrating loss of WAT. FIG. 7 shows serum adiponectin levels determined by immunoblotting with anti-adiponectin antibody through use of recombinant adiponectin as standards. In FIG. 7, lane 9 shows the serum adiponectin level when 50 μg of Ad was administered to mice through intraperitoneal (ip) injection. FIG. 8 shows insulin resistance indices. The results are expressed as the percentage of the value based on that of untreated PPAR-γ$^{+/-}$ mice on the high-fat diet. The basal glucose level (time=0 of the glucose tolerance test) of untreated PPAR-γ$^{+/-}$ mice on the high-fat diet was 110.7±12.8 mg/dl. Each bar represents the mean±s.e. (n=5-10) (*, P<0.05; **, P<0.01; compared with PPAR-γ$^{+/-}$ mice untreated or treated with HX531 alone for six weeks or with PPAR-γ$^{+/-}$ mice treated with both leptin and adiponectin).

As a result, administration of a PPAR-γ/RXR inhibitor such as an RXR antagonist HX531 to PPAR-γ$^{+/-}$ mice for three weeks markedly lowered expression of genes responsive to PPAR-γ/RXR, such as lipoprotein lipase (LPL) in WAT (about 90% or further; FIG. 4), indicating that PPAR-γ/RXR activity was likely to be significantly decreased. Four weeks of this treatment resulted in disappearance of visible WAT (FIGS. 5 and 6). This loss of fat tissue presumably results from lowered expression of molecules involved in triglyceride accumulation in WAT, the expression of which is dependent on PPAR-γ/RXR activity.

Adiponectin was completely absent in sera from the lipoatrophic mice, whereas adiponectin was detected as a 35-kD protein with an antibody against adiponectin in sera from control mice (FIG. 7, lanes 6 and 7).

Tissue triglyceride content and free fatty acid in serum in the lipoatrophic mice were also determined.

While PPAR-γ$^{+/-}$ mice were treated with HX531 for six weeks (+) or untreated (−), recombinant full-length adiponectin (Ad), gAd, or leptin (Lep) was administered to each PPAR-γ$^{+/-}$ mouse at a predetermined dose (μg/day). Administration was performed through continuous systemic infusion in combination with the high-fat (HF) diet for the final twelve days of the six-week HX531 treatment (six weeks).

The lipoatrophic mice showed increased serum free fatty acid (FFA) levels, increased triglyceride levels, increased tissue triglyceride content in skeletal muscle and liver (Table 1) as well as hyperinsulinemia and hyperglycemia (FIG. 8).

TABLE 1

Tissue triglyceride content and serum free fatty acid level in lipoatrophic mice

|  | — | | HX531 | | |
| --- | --- | --- | --- | --- | --- |
|  | — | Ad50 | — | Ad50 | gAd2.5 |
| Skeletal muscle TG content (mg/g tissue) | 6.24 ± 0.43 | 5.47 ± 0.32* | 15.96 ± 1.47 | 7.74 ± 0.65** | 3.88 ± 1.74** |
| Liver TG content (mg/g tissue) | 8.02 ± 1.18 | 6.45 ± 0.26* | 19.36 ± 1.23 | 16.19 ± 0.72** | 13.81 ± 0.91** |
| Serum FFA (mEq/L) | 0.42 ± 0.03 | 0.35 ± 0.02* | 1.48 ± 0.25 | 0.61 ± 0.13** | 0.43 ± 0.14** |
| Serum TG (mg/dl) | 82.6 ± 8.9 | 60.5 ± 6.0* | 201.4 ± 25.3 | 106.6 ± 18.1** | 100.3 ± 17.5** |

Mean ± s.e. (n = 5-10),
*P < 0.05,
**P < 0.01 (compared with untreated mice or mice treated with HX531 alone for 6 weeks)

(3) Reversal of Insulin Resistance of Lipoatrophic Mice by Use of Adiponectin

To determine the role of adiponectin deficiency in the development of insulin resistance in lipoatrophic mice, adiponectin was administered to the mice. Continuous systemic infusion of recombinant adiponectin at a physiological concentration (FIG. 7, lanes 6 to 8) significantly ameliorated hyperglycemia and hyperinsulinemia (FIG. 8).

(4) Effect of Globular Domain of Adiponectin

Adiponectin is composed of an N-terminal collagen-like sequence (cAd) and a C-terminal globular domain (gAd) (see SEQ ID NO: 1). An analysis was performed to determine which domain exerts these physiological effects. As a result, gAd ameliorated hyperglycemia and hyperinsulinemia much more potently than full-length adiponectin (FIG. 8). A 25-kD protein recognized by an antibody against C-terminal portion of adiponectin was present in the serum, albeit in a very small amount, suggesting that full-length adiponectin might undergo proteolytic processing.

(5) Improvement of Insulin Resistance Through Adiponectin/Leptin Deficiency

Insulin resistance in lipoatrophic diabetes might be due to deficiency of adipocytokines which sensitize tissues to insulin. The above results indicate that adiponectin is one of such adipocytokines. Administration of adiponectin at a physiological concentration was not sufficient to completely ameliorate insulin resistance in mice without adipose tissue. Leptin has also been known to be such an adipocytokine. Serum leptin levels were undetectable in these mice (upper limit: 0.2 ng/ml). Administration of leptin to these mice at a physiological concentration did indeed alleviate their insulin resistance, albeit partially (FIG. 8). Administration of adiponectin and leptin in combination at a physiological concentration almost completely removed insulin resistance synergistically (FIG. 8).

(6) Decrease in Tissue Triglyceride Content Caused by Adiponectin

To determine the mechanism by which adiponectin exerts effects of treating diabetes, effects of adiponectin in individual organs were investigated.

Figure 9:
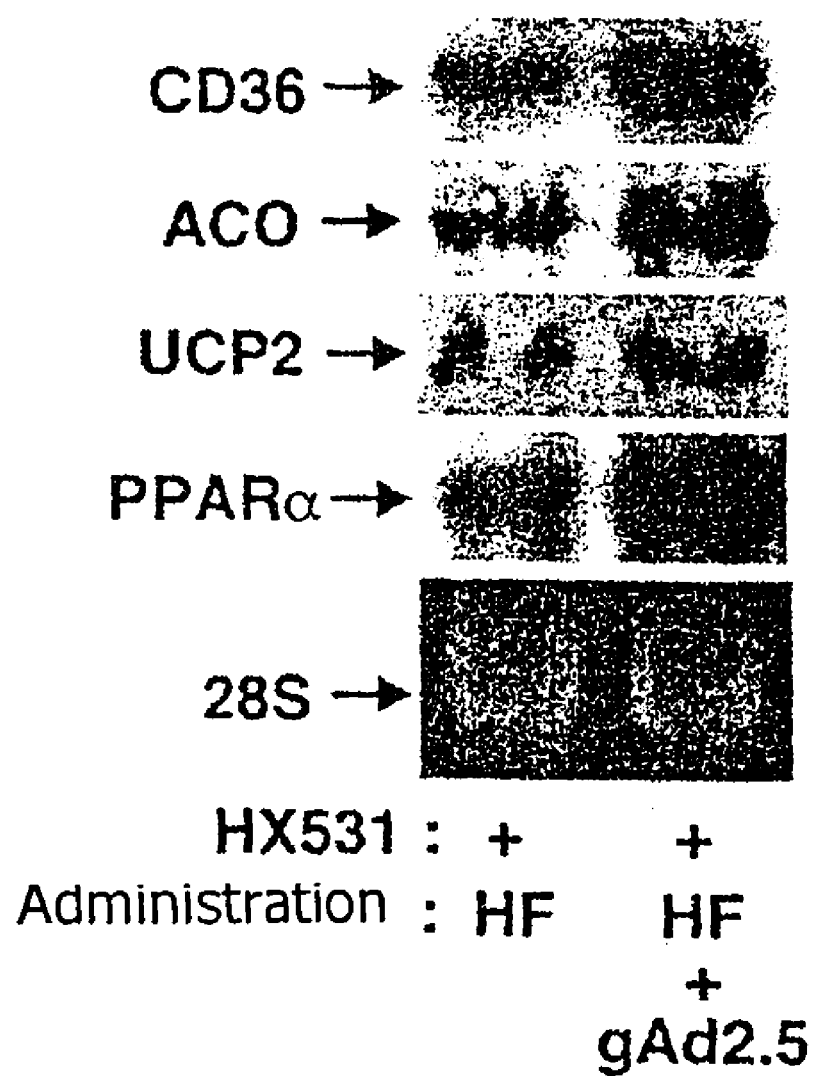
FIG. 9 shows expression of mRNAs of CD36, ACO, UCP2, and PPAR-$\alpha$ in the mouse skeletal muscle.
Figure 10:
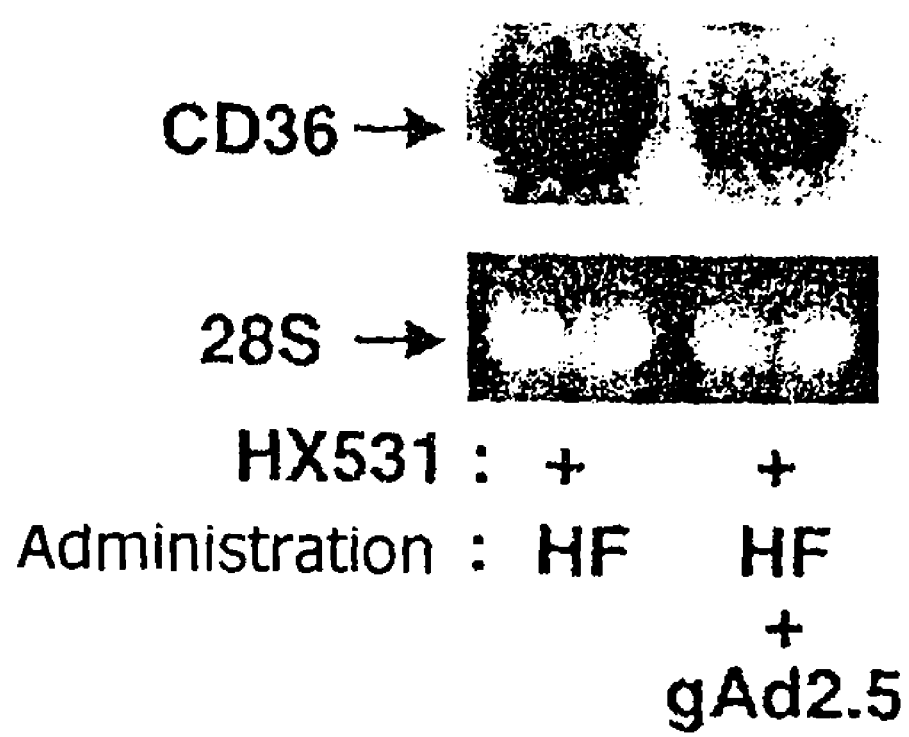
FIG. 10 shows expression of mRNAs of CD36, ACO, UCP2, and PPAR-$\alpha$ in the mouse liver.
Figure 11:
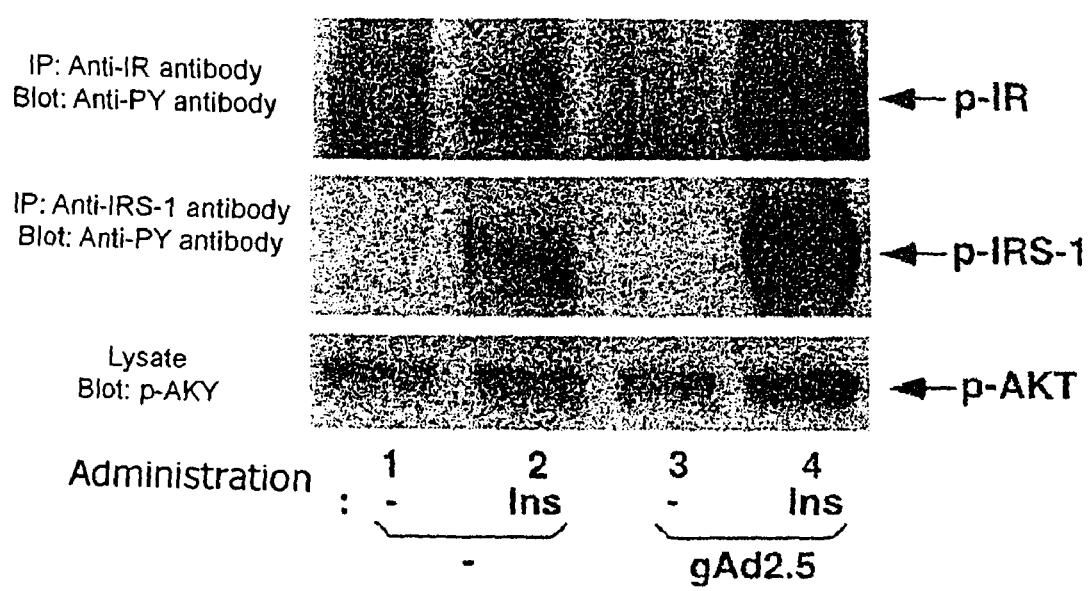
FIG. 11 shows insulin-induced tyrosine phosphorylation and insulin (Ins)-stimulated phosphorylation of Akt of insulin receptor (IR) and insulin receptor substrate (IRS)-1 in the mouse skeletal muscle.

FIGS. 9 and 10 show mRNAs of fatty-acid translocase (FAT)/CD36, ACO, UCP2, and PPAR-α in mouse skeletal muscle and in liver, respectively. FIG. 11 shows insulin-induced tyrosine phosphorylation of insulin receptor (IR) and insulin receptor substrate (IRS)-1 in skeletal muscle, and insulin-stimulated phosphorylation of Akt in skeletal muscle. HX531 was administered as a 0.1% food admixture. Mice were stimulated with or without 1 U/g body weight of insulin for two minutes. Lysates were subjected to immunoprecipitation (IP) and immunoblotting through use of the antibodies described in Mol. Cell. Biol. 16, 1074-3084 (1996).

As a result, in skeletal muscle, administration of gAd at a low concentration increased expression of molecules involved in fatty-acid transport, combustion and energy dissipation such as CD36, acyl-CoA oxidase (ACO), and uncoupling protein (UCP)2, respectively (FIG. 9). In turn, these processes lead to decreased tissue triglyceride content in skeletal muscle (Table 1). Expression of these genes has been known to be positively controlled by PPAR. Therefore, possible mechanism(s) underlying these alterations in gene expression might include increased expression of PPAR-α/γ and/or increased endogenous ligands. Indeed, expression of PPAR-α was increased (FIG. 9). In contrast to skeletal muscle, in the liver, administration of gAd at a low concentration decreased the expression of molecules involved in fatty-acid transport into tissues such as CD36 (FIG. 10), thereby reducing fatty-acid influx into the liver, which might lead to decrease in hepatic triglyceride content in the liver (Table 1). Thus, even though triglyceride content was decreased in both muscle and liver, the mechanisms involved in the decrease in triglyceride content are apparently quite different in the two tissues. These data indicate that adiponectin acts primarily on skeletal muscle to increase influx and combustion of FFA, thereby reducing muscle triglyceride content. As a consequence of decreased serum FFA and triglyceride levels (Table 1), hepatic triglyceride content is decreased.

(7) Improvement of Insulin Signaling Caused by Decrease of Triglyceride Content

Increased tissue triglyceride content has been reported to interfere with insulin-stimulated activation of phosphatidylinositol-3-kinase and subsequent translocation of glucose-transporter protein 4 to surfaces of cell membrane and uptake of glucose, which leads to development of insulin resistance. Thus, decreased triglyceride content in muscle might contribute to the improved insulin signal transduction, as demonstrated by increase in insulin-induced tyrosine phosphorylation of insulin receptor and insulin-receptor substrate 1, as well as increases in insulin-stimulated phosphorylation of Akt kinase in skeletal muscle of adiponectin-administered lipoatrophic mice (FIG. 11).

(8) Effect of Adiponectin on Improvement of Insulin Resistance in Obese Mice

Next, studies were performed to investigate whether adiponectin can improve insulin resistance and diabetes in db/db and KKA$^y$ mice (KK mice overexpressing agouti), two different mouse models of type 2 diabetes characterized by obesity, hyperlipidemia, insulin resistance, and hyperglycemia.

Figure 13:
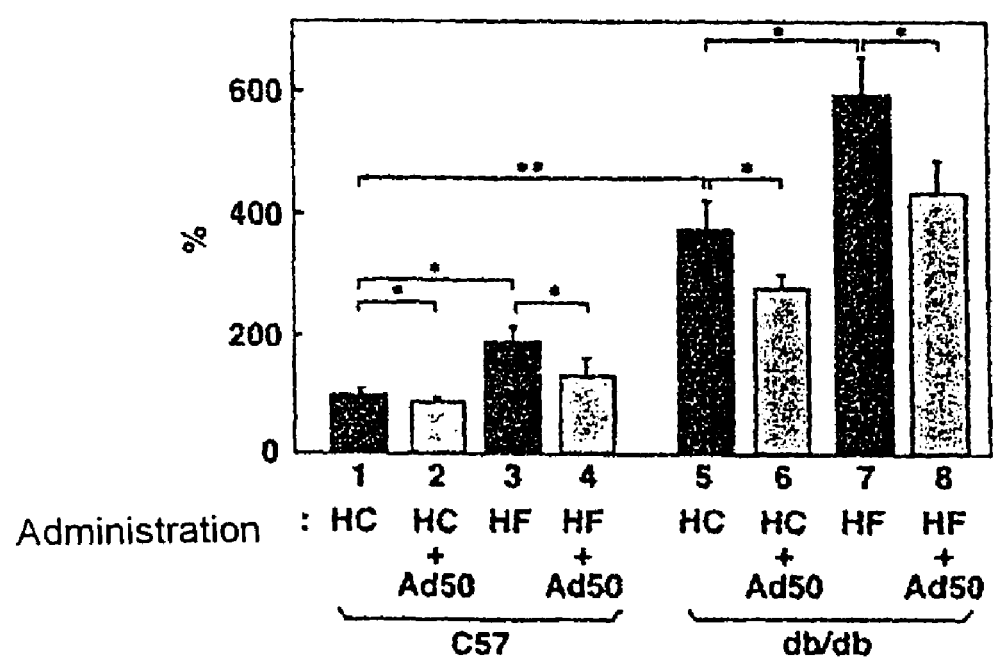
FIG. 13 shows the calculated areas under the glucose curves obtained through glucose tolerance test of C57 and db/db mice.
Figure 14:
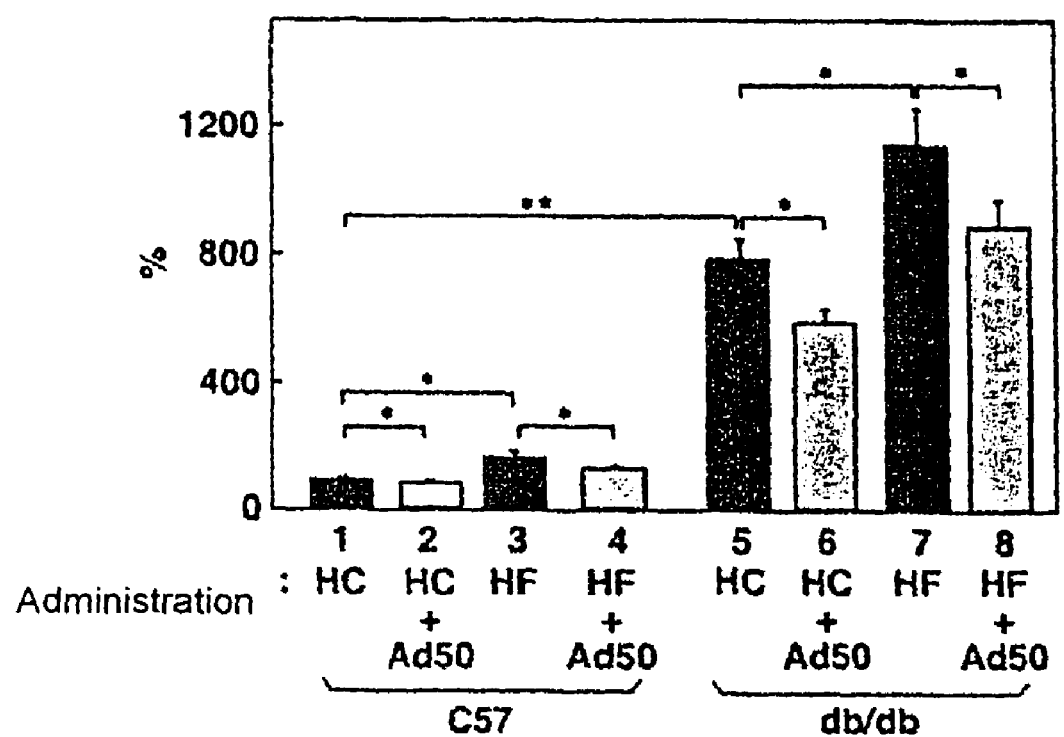
FIG. 14 shows calculated areas under the insulin curves obtained through glucose tolerance test of C57 and db/db mice.
Figure 15:
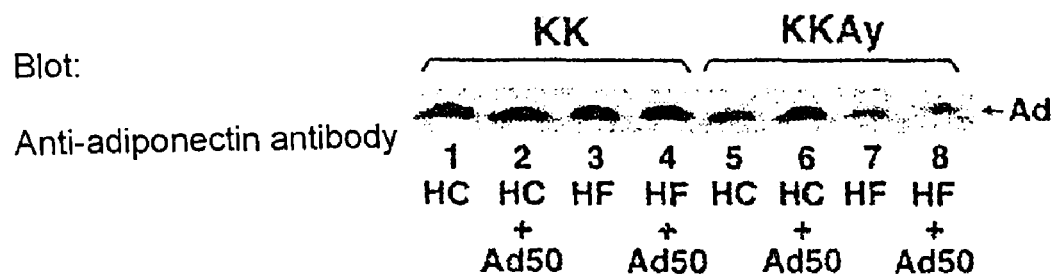
FIG. 15 shows serum adiponectin levels obtained through a glucose tolerance test of KK and KKA$^y$ mice.
Figure 16:
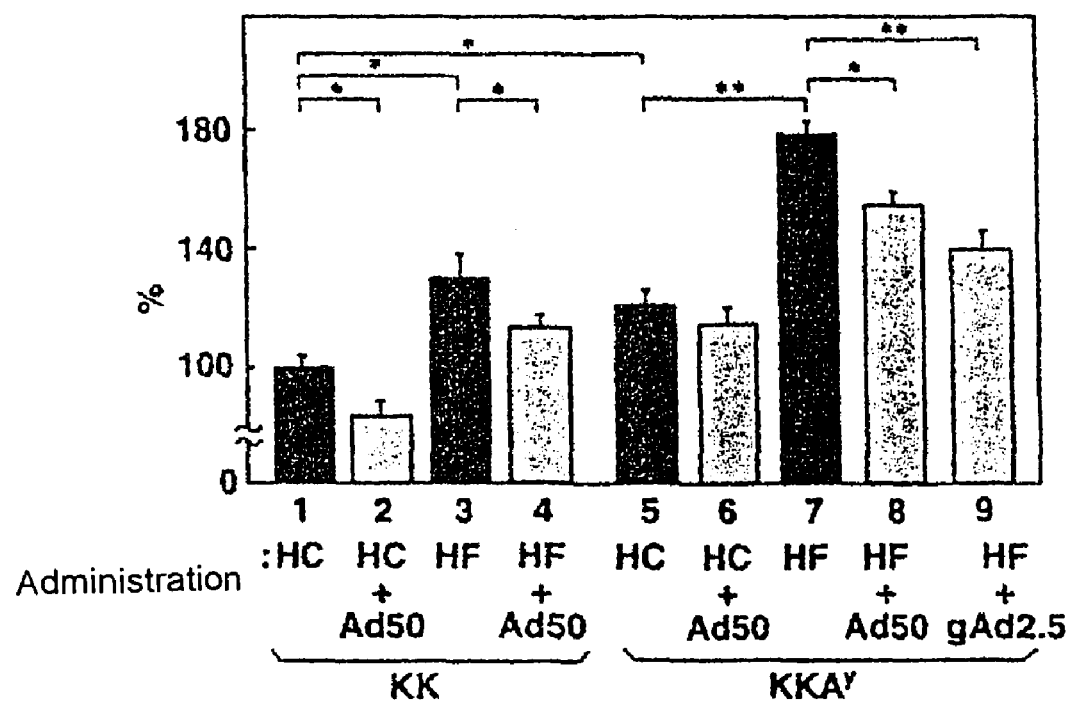
FIG. 16 shows calculated areas under the glucose curves obtained through a glucose tolerance test of KK and KKA$^y$ mice.
Figure 17:
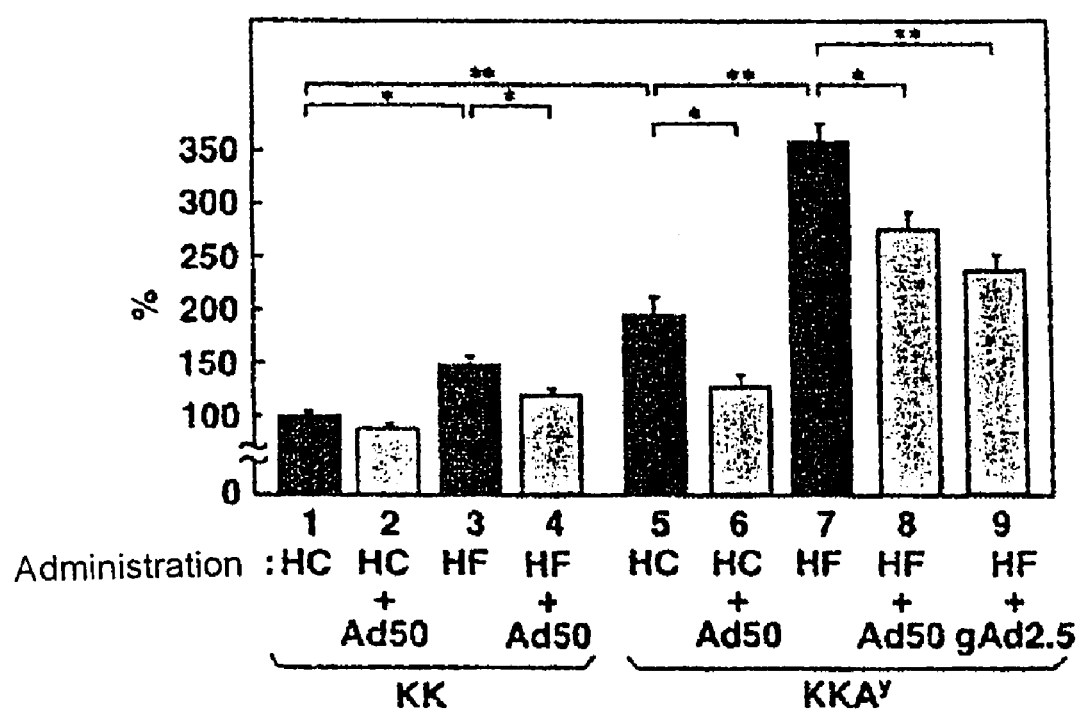
FIG. 17 shows calculated areas under the insulin curves obtained through a glucose tolerance test of KK and KKA$^y$ mice.

The results are shown in FIGS. 12 to 17: serum levels of adiponectin (FIGS. 12 and 15), areas under the glucose curve (FIGS. 13 and 16), and areas under the insulin curve (FIGS. 14 and 17), obtained through glucose tolerance test (GTT) of C57 or db/db mice (FIGS. 12 to 14) or of KK or KKA$^y$ mice (FIGS. 15 to 17). The mice were fed an HC or HF diet. In addition, Ad or gAd was administered, or none of these was administered, to the mice at a predetermined dose (µg/day).

Figure 12:
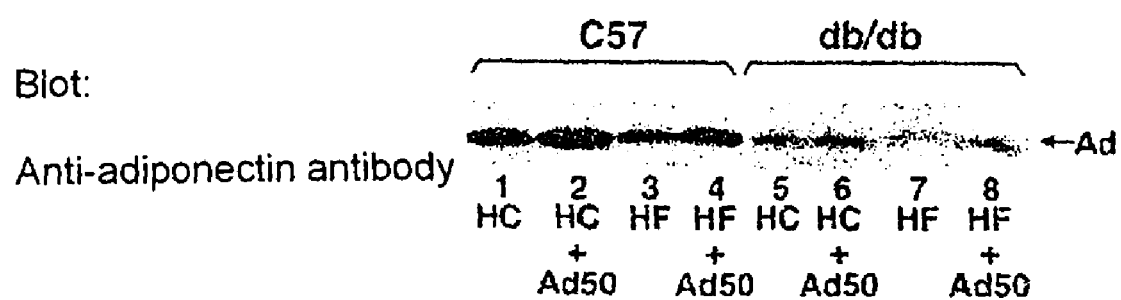
FIG. 12 shows serum adiponectin levels obtained through a glucose tolerance test of C57 and db/db mice.

Serum adiponectin levels were determined by immunoblotting with anti-adiponectin antibody through use of a recombinant adiponectin as standards (FIGS. 12 and 15). The results are expressed as the percentage of the value based on untreated wild-type mice on the HC diet (FIGS. 13, 14, 16, and 17). The basal glucose level (time=0 of the GTT) of untreated C57 mice on the HC diet was found to be 62.3±3.1 mg/dl (FIG. 13), and that of KK mice was found to be 93.0±6.1 mg/dl (FIG. 16). Each bar represents the mean±s.e. (n=5-10) (*, P<0.05; **, P<0.01; C57 versus db/db, KK versus KKA$^y$, or HC versus HF, or compared with untreated mice).

As a result, serum adiponectin levels were decreased in wild-type mice on a high-fat diet (FIG. 12, lane 3) as compared with those in mice on a high-carbohydrate diet (FIG. 12, lane 1). Serum adiponectin levels in db/db mice (FIG. 12, lanes 5 and 7) were also decreased as compared with wild-type controls on either high-carbohydrate or high-fat diet (FIG. 12, lanes 1 and 3). Lower serum adiponectin levels in wild-type mice on the high-fat diet were partially restored to those of wild-type controls on the high-carbohydrate diet by continuous systemic infusion of low doses of recombinant adiponectin (FIG. 12, lanes 1, 3, and 4). The infusion also significantly ameliorated hyperglycemia and hyperinsulinemia (FIG. 14, lanes 1, 3, and 4) induced by high-fat diet (FIG. 13, lanes 1, 3, and 4). Lower serum adiponectin levels in db/db mice on either high-carbohydrate or high-fat diet were also partially restored to those in respective wild-type controls by the adiponectin replenishment (FIG. 12), which also significantly ameliorated leptin receptor deficiency-induced hyperglycemia (FIG. 13) and hyperinsulinemia (FIG. 14). We obtained similar results when using KKA$^y$ mice and their wild-type controls (FIGS. 15 to 17). These data indicate that high-fat feeding, leptin-receptor deficiency, or agouti overexpression causes insulin resistance, partially through decreases in adiponectin, and that adiponectin is useful as an anti-diabetic drug.

In addition, effect of administration of adiponectin on fatty acid oxidation in the skeletal muscle of KKA$^y$ mice was studied.

The following values were determined through use of KKA$^y$ mice: acyl-CoA oxidase (ACO) activity and fatty acid oxidation in the skeletal muscle and in the liver, tissue triglyceride content in the skeletal muscle and in the liver, and serum free fatty acid level and serum triglyceride level. Mice were fed with high fat diet, and full-length adiponectin (Ad) or adiponectin globular domain (gAd) was administered to each mice at a dose shown in Table 2 for two weeks.

The results are shown in Table 2.

TABLE 2

| | | — | Ad50 | gAd2.5 |
|---|---|---|---|---|
| ACO activity | skeletal muscle | 0.24 ± 0.02 | 0.37 ± 0.04* | 0.42 ± 0.04** |
| (nmol/mg/min) | liver | 3.21 ± 0.33 | 3.04 ± 0.85 | 2.89 ± 0.35 |
| Fatty acid oxidation | skeletal muscle | 2.52 ± 0.23 | 3.95 ± 0.58* | 4.06 ± 0.44* |
| [$^{14}$C] palmitate→$CO_2$ | liver | 3.31 ± 0.38 | 2.92 ± 0.29 | 2.89 ± 0.21 |
| (nmol/g/h) | | | | |
| TG content | skeletal muscle | 10.94 ± 1.03 | 8.75 ± 0.58* | 8.06 ± 0.61* |
| (mg/g tissue) | liver | 19.07 ± 1.78 | 16.15 ± 0.83* | 16.04 ± 0.91* |
| Serum FFA (mEq/L) | | 1.29 ± 0.12 | 0.67 ± 0.09** | 0.39 ± 0.04** |
| Serum TG (mg/dl) | | 200.2 ± 20.8 | 101.3 ± 19.7** | 96.4 ± 18.3** |
| Rectal temperature (° C.) | | 36.7 ± 0.3 | 37.3 ± 0.2* | 37.7 ± 0.1** |

Mean ± s.e. (n = 5-10),
*P < 0.05,
**P < 0.01 (compared with untreated mice)

(9) Facilitation of β-Oxidation by Adiponectin

In skeletal muscle, adiponectin-administered KKA$^y$ mice showed increased expression of enzymes involved in β-oxidation and UCP2. In mice to which adiponectin had been administered, ACO activities and fatty-acid combustion were increased in skeletal muscle but not liver (Table 2). These alterations decreased triglyceride content in skeletal muscle, and also decreased serum FFA and triglyceride levels (Table 2). These reductions in serum FFA and triglyceride levels seem to cause subsequent decreased expression of molecules involved in fatty-acid transport into hepatic tissues, thereby also reducing tissue triglyceride content in liver (Table 2).

In contrast, administration of adiponectin to normal C57 mice for two weeks slightly, but not significantly, reduced the increases in WAT weight (untreated mice: 0.53±0.03 g; gAd-treated: 0.48±0.04 g) and body weight associated with the high-fat diet as compared with vehicle (vehicle-treated: 22.8±2.0 g; gAd-treated: 20.6±2.1 g). Food intake tended to be higher in adiponectin-treated mice as compared with the control on the high-fat diet (vehicle-treated: 5.71±0.56 g/day; gAd-treated: 6.28±0.51 g/day), and the rectal temperature was significantly higher in mice to which adiponectin had been administered (Table 2), consistent with increased expression of molecules involved in fatty-acid combustion and energy dissipation in muscle and brown adipose tissue. However, the anti-diabetic effects of adiponectin were not attenuated in db/db mice, which lack leptin receptor (FIGS. 12 to 14). Moreover, administration of adiponectin to wild-type mice did not alter the expression of leptin in WAT and serum leptin levels (vehicle: 11.1±2.1 ng/ml; gAd: 10.4±2.6 ng/ml). We obtained essentially similar results of serum leptin levels by using KK (vehicle: 15.1±2.5 ng/ml; gAd-treated: 13.4±2.7 ng/ml), KKA$^y$ (vehicle: 61.5±5.4 ng/ml; gAd-treated: 57.9±5.7 ng/ml), and db/db mice (vehicle: 153.9±20.4 ng/ml; gAd-treated: 145.2±14.7 ng/ml). These findings indicate that adiponectin exerted effects of treating diabetic through leptin-independent pathways.

INDUSTRIAL APPLICABILITY

The present invention reverses insulin resistance induced from a high fat diet and associated with obesity, and therefore, enables treatment of type 2 diabetes, which is the most common among other types of diabetes.

What we claim is:

1. A method for treating insulin resistance in a subject in need thereof comprising administering an effective amount of an agent containing, as an active component, a C-terminal globular domain of adiponectin consisting of amino acid residues 111 to 242 of SEQ ID NO: 2 or 114 to 239 of SEQ ID NO: 2.

2. The method of claim 1, wherein said agent further comprises a pharmacologically acceptable carrier.

3. The method of claim 2, wherein said pharmacologically acceptable carrier is selected from the group consisting of distilled water, a solubilizer, a stabilizer, an emulsifier, and a buffer.

4. The method of claim 1, wherein said administering is by injection.

5. The method of claim 1, wherein said effective amount ranges from 0.1 μg/day to 10 mg/day based on the amount of adiponectin.

6. The method of claim 1, wherein said C-terminal globular domain of adiponectin consists of amino acid residues 111 to 242 of SEQ ID NO: 2.

7. The method of claim 1, wherein said C-terminal globular domain of adiponectin consists of amino acid residues 114 to 239 of SEQ ID NO: 2.

8. A method for treating type 2 diabetes in a subject in need thereof comprising administering an effective amount of a therapeutic agent for type 2 diabetes containing, as an active component, a C-terminal globular domain of adiponectin consisting of amino acid residues 111 to 242 of SEQ ID NO: 2 or 114 to 239 of SEQ ID NO: 2.

9. The method of claim 8, wherein said agent further comprises a pharmacologically acceptable carrier.

10. The method of claim 9, wherein said pharmacologically acceptable carrier is selected from the group consisting of distilled water, a solubilizer, a stabilizer, an emulsifier, and a buffer.

11. The method of claim 8, wherein said administering is by injection.

12. The method of claim 8, wherein said effective amount ranges from 0.1 µg/day to 10 mg/day.

13. The method of claim 8, wherein said C-terminal globular domain of adiponectin consists of amino acid residues 111 to 242 of SEQ ID NO: 2.

14. The method of claim 8, wherein said C-terminal globular domain of adiponectin consists of amino acid residues 114 to 239 of SEQ ID NO: 2.

\* \* \* \* \*

SEQUENCE LISTING

```
<160> NUMBER OF SEQ ID NOS: 4

<210> SEQ ID NO 1
<211> LENGTH: 735
<212> TYPE: DNA
<213> ORGANISM: Homo sapiens
<220> FEATURE:
<221> NAME/KEY: CDS
<222> LOCATION: (1)..(735)

<400> SEQUENCE: 1 atg ctg ttg ctg gga gct gtt cta ctg cta tta gct ctg ccc ggt cat       48
Met Leu Leu Leu Gly Ala Val Leu Leu Leu Leu Ala Leu Pro Gly His
1               5                   10                  15 gac cag gaa acc acg act caa ggg ccc gga gtc ctg ctt ccc ctg ccc       96
Asp Gln Glu Thr Thr Thr Gln Gly Pro Gly Val Leu Leu Pro Leu Pro
            20                  25                  30 aag ggg gcc tgc aca ggt tgg atg gcg ggc atc cca ggg cat ccg ggc      144
Lys Gly Ala Cys Thr Gly Trp Met Ala Gly Ile Pro Gly His Pro Gly
        35                  40                  45 cat aat ggg gcc cca ggc cgt gat ggc aga gat ggc acc cct ggt gag      192
His Asn Gly Ala Pro Gly Arg Asp Gly Arg Asp Gly Thr Pro Gly Glu
    50                  55                  60 aag ggt gag aaa gga gat cca ggt ctt att ggt cct aag gga gac atc      240
Lys Gly Glu Lys Gly Asp Pro Gly Leu Ile Gly Pro Lys Gly Asp Ile
65                  70                  75                  80 ggt gaa acc gga gta ccc ggg gct gaa ggt ccc cga ggc ttt ccg gga      288
Gly Glu Thr Gly Val Pro Gly Ala Glu Gly Pro Arg Gly Phe Pro Gly
                85                  90                  95 atc caa ggc agg aaa gga gaa cct gga gaa ggt gcc tat gta tac cgc      336
Ile Gln Gly Arg Lys Gly Glu Pro Gly Glu Gly Ala Tyr Val Tyr Arg
            100                 105                 110 tca gca ttc agt gtg gga ttg gag act tac gtt act atc ccc aac atg      384
Ser Ala Phe Ser Val Gly Leu Glu Thr Tyr Val Thr Ile Pro Asn Met
        115                 120                 125 ccc att cgc ttt acc aag atc ttc tac aat cag caa aac cac tat gat      432
Pro Ile Arg Phe Thr Lys Ile Phe Tyr Asn Gln Gln Asn His Tyr Asp
    130                 135                 140 ggc tcc act ggt aaa ttc cac tgc aac att cct ggg ctg tac tac ttt      480
Gly Ser Thr Gly Lys Phe His Cys Asn Ile Pro Gly Leu Tyr Tyr Phe
145                 150                 155                 160 gcc tac cac atc aca gtc tat atg aag gat gtg aag gtc agc ctc ttc      528
Ala Tyr His Ile Thr Val Tyr Met Lys Asp Val Lys Val Ser Leu Phe
                165                 170                 175 aag aag gac aag gct atg ctc ttc acc tat gat cag tac cag gaa aat      576
Lys Lys Asp Lys Ala Met Leu Phe Thr Tyr Asp Gln Tyr Gln Glu Asn
            180                 185                 190 aat gtg gac cag gcc tcc ggc tct gtg ctc ctg cat ctg gag gtg ggc      624
Asn Val Asp Gln Ala Ser Gly Ser Val Leu Leu His Leu Glu Val Gly
        195                 200                 205 gac caa gtc tgg ctc cag gtg tat ggg gaa gga gag cgt aat gga ctc      672
```

```
Asp Gln Val Trp Leu Gln Val Tyr Gly Glu Gly Glu Arg Asn Gly Leu
    210                 215                 220 tat gct gat aat gac aat gac tcc acc ttc aca ggc ttt ctt ctc tac      720
Tyr Ala Asp Asn Asp Asn Asp Ser Thr Phe Thr Gly Phe Leu Leu Tyr
225                 230                 235                 240 cat gac acc aac tga                                                  735
His Asp Thr Asn
```

<210> SEQ ID NO 2
<211> LENGTH: 244
<212> TYPE: PRT
<213> ORGANISM: Homo sapiens

<400> SEQUENCE: 2

```
Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
        130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn
```

<210> SEQ ID NO 3
<211> LENGTH: 1276
<212> TYPE: DNA
<213> ORGANISM: Mus musculus
<220> FEATURE:
<221> NAME/KEY: CDS
<222> LOCATION: (46)..(789)

<400> SEQUENCE: 3

```
ctctaaagat tgtcagtgga tctgacgaca ccaaaagggc tcagg atg cta ctg ttg     57
                                                Met Leu Leu Leu
                                                1
```

| | | |
|---|---|---|
| caa gct ctc ctg ttc ctc tta atc ctg ccc agt cat gcc gaa gat gac<br>Gln Ala Leu Leu Phe Leu Leu Ile Leu Pro Ser His Ala Glu Asp Asp<br>5                           10                     15                  20 | 105 |
| gtt act aca act gaa gag cta gct cct gct ttg gtc cct cca ccc aag<br>Val Thr Thr Thr Glu Glu Leu Ala Pro Ala Leu Val Pro Pro Pro Lys<br>                      25                     30                     35 | 153 |
| gga act tgt gca ggt tgg atg gca ggc atc cca gga cat cct ggc cac<br>Gly Thr Cys Ala Gly Trp Met Ala Gly Ile Pro Gly His Pro Gly His<br>             40                        45                     50 | 201 |
| aat ggc aca cca ggc cgt gat ggc aga gat ggc act cct gga gag aag<br>Asn Gly Thr Pro Gly Arg Asp Gly Arg Asp Gly Thr Pro Gly Glu Lys<br>          55                     60                     65 | 249 |
| gga gag aaa gga gat gca ggt ctt ctt ggt cct aag ggt gag aca gga<br>Gly Glu Lys Gly Asp Ala Gly Leu Leu Gly Pro Lys Gly Glu Thr Gly<br>70                          75                     80 | 297 |
| gat gtt gga atg aca gga gct gaa ggg cca cgg ggc ttc ccc gga acc<br>Asp Val Gly Met Thr Gly Ala Glu Gly Pro Arg Gly Phe Pro Gly Thr<br>85                          90                     95               100 | 345 |
| cct ggc agg aaa gga gag cct gga gaa gcc gct tat atg tat cgc tca<br>Pro Gly Arg Lys Gly Glu Pro Gly Glu Ala Ala Tyr Met Tyr Arg Ser<br>                    105                     110                     115 | 393 |
| gcg ttc agt gtg ggg ctg gag acc cgc gtc act gtt ccc aat gta ccc<br>Ala Phe Ser Val Gly Leu Glu Thr Arg Val Thr Val Pro Asn Val Pro<br>                 120                     125                     130 | 441 |
| att cgc ttt act aag atc ttc tac aac caa cag aat cat tat gac ggc<br>Ile Arg Phe Thr Lys Ile Phe Tyr Asn Gln Gln Asn His Tyr Asp Gly<br>                 135                     140                     145 | 489 |
| agc act ggc aag ttc tac tgc aac att ccg gga ctc tac tac ttc tct<br>Ser Thr Gly Lys Phe Tyr Cys Asn Ile Pro Gly Leu Tyr Tyr Phe Ser<br>150                        155                     160 | 537 |
| tac cac atc acg gtg tac atg aaa gat gtg aag gtg agc ctc ttc aag<br>Tyr His Ile Thr Val Tyr Met Lys Asp Val Lys Val Ser Leu Phe Lys<br>165                        170                     175                     180 | 585 |
| aag gac aag gcc gtt ctc ttc acc tac gac cag tat cag gaa aag aat<br>Lys Asp Lys Ala Val Leu Phe Thr Tyr Asp Gln Tyr Gln Glu Lys Asn<br>                 185                     190                     195 | 633 |
| gtg gac cag gcc tct ggc tct gtg ctc ctc cat ctg gag gtg gga gac<br>Val Asp Gln Ala Ser Gly Ser Val Leu Leu His Leu Glu Val Gly Asp<br>                    200                     205                     210 | 681 |
| caa gtc tgg ctc cag gtg tat ggg gat ggg gac cac aat gga ctc tat<br>Gln Val Trp Leu Gln Val Tyr Gly Asp Gly Asp His Asn Gly Leu Tyr<br>               215                     220                     225 | 729 |
| gca gat aac gtc aac gac tct aca ttt act ggc ttt ctt ctc tac cat<br>Ala Asp Asn Val Asn Asp Ser Thr Phe Thr Gly Phe Leu Leu Tyr His<br>          230                     235                     240 | 777 |
| gat acc aac tga ctgcaactac ccatagccca tacaccagga gaatcatgga<br>Asp Thr Asn<br>245 | 829 |
| acagtcgaca cactttcagc ttagtttgag agattgattt tattgcttag tttgagagtc | 889 |
| ctgagtatta tccacacgtg tactcacttg ttcattaaac gactttataa aaaataattt | 949 |
| gtgttcctag tccagaaaaa aaggcactcc ctggtctcca cgactcttac atggtagcaa | 1009 |
| taacagaatg aaaatcacat ttggtatggg ggcttcacaa tattcgcatg actgtctgga | 1069 |
| agtagaccat gctattttc tgctcactgt acacaaatat tgttcacata aaccctataa | 1129 |
| tgtaaatatg aaatacagtg attactcttc tcacaggctg agtgtatgaa tgtctaaaga | 1189 |
| cccataagta ttaaagtggt agggataaat tggaaaaaaa aaaaaaaaaa aagaaaaact | 1249 |

```
-continued ttagagcaca ctggcggccg ttactag                                         1276

<210> SEQ ID NO 4
<211> LENGTH: 247
<212> TYPE: PRT
<213> ORGANISM: Mus musculus

<400> SEQUENCE: 4

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
            115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
            165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
            195                 200                 205

Glu Val Gly Asp Gln Val Trp Leu Gln Val Tyr Gly Asp Gly Asp His
210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245
```